US00PP27620P2

(12) United States Plant Patent
Kordes

(10) Patent No.: US PP27,620 P2
(45) Date of Patent: Jan. 31, 2017

(54) MINIATURE ROSE PLANT NAMED 'KORPOT062'

(50) Latin Name: *Rosa hybrida*
Varietal Denomination: KORpot062

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 106 days.

(21) Appl. No.: 14/544,529

(22) Filed: Jan. 14, 2015

(51) Int. Cl.
*A01H 5/02* (2006.01)

(52) U.S. Cl.
USPC ..... Plt./118

(58) Field of Classification Search
USPC ..... Plt./116, 118
See application file for complete search history.

*Primary Examiner* — Susan McCormick Ewoldt

(57) ABSTRACT

A new and distinct variety of rose with long lasting, novel yellow flowers, and attractive foliage with above average disease resistance. It exhibits compact, bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORpot062'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a miniature rose plant which was discovered in a cultivated area in my nursery in June 2013. The new rose variety resulted from a naturally occurring mutation of unknown causation on a branch of 'KORbailand', a rose variety from the same inventor described and illustrated in U.S. Plant Pat. No. 23,845 and issued on Aug. 27, 2013.

The new rose plant was asexually propagated for further evaluation. This new and distinctive rose variety is named 'KORpot062'.

SUMMARY OF THE INVENTION

The new rose plant may be distinguished from its seed parent, an 'KORbailand', by the following combination of characteristics:

1. 'KORpot062' has yellow flowers, whereas 'KORbailand' has apricot-orange colored flowers.
2. 'KORpot062' has slightly larger flowers than 'KORbailand'.

The new and distinct rose plant was selected due to it its:

1. Compact and uniform growth and flowering under greenhouse conditions when grown as a potted floral plant;

2. Abundant, long lasting, and attractive yellow flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot062' from all other varieties of which I am aware.

As part of the rose evaluation program, Tim-Hermann Kordes asexually propagated the mutation by rooting cuttings, and conducted evaluations and observations on the resulting plants in a controlled environment in Offenseth-Sparrieshoop, Germany. The resulting seedlings exhibited distinctive physical and biological characteristics. The first asexual reproduction of 'KORpot062' was done by rooting softwood cuttings in a controlled environment in June 2013 at the inventor's nursery in Offenseth-Sparrieshoop, Germany.

These initial and other subsequent propagations conducted in controlled environments demonstrate that 'KORpot062' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot062'.

DETAILED BOTANICAL DESCRIPTION

The following is a description of 'KORpot062', as observed growing in November 2014 in a nursery in Jackson County, Oreg. on plants of 6 months of age. Color references are made using The Royal Horticultural Society (London, England) Colour Chart, 2001 except where common terms of color are used.

For a comparison, several physical characteristics of the rose variety 'KORbailand', a rose variety from the same inventor described and illustrated in U.S. Plant Pat. No. 23,845 and issued on Aug. 27, 2013 are compared to 'KORpot062' in Chart 1.

CHART 1

| Characteristic | 'KORpot062' | 'KORbailand' |
|---|---|---|
| Average open flower height. | 20 to 25 mm. | 15 mm. |
| General tonality of open flower. | Yellow-Orange Group 15C. | Red Group 40D. |
| Petal count. | Average of 90 petals under normal conditions. | Average of 25 to 35 petals under normal conditions. |

Parents:

*Parent*.—'KORbailand.'

Classification:

*Botanical classification*.—*Rosa hybrida* 'KORpot062'.

*Commercial classification*.—Miniature rose.

FLOWER AND FLOWER BUD

Blooming habit: Recurrent.

Flower bud:

*Size*.—Upon opening, 25 mm in length from base of receptacle to distal end of bud and 10 to 15 mm diameter at its widest point.

*Bud form*.—Pointed ovoid.

*Bud color*.—As sepals first unfold, bud color is Orange Group 24B. When ¼ open, upper surface of petals: Marginal Zone: Yellow Group 10C. Middle Zone: Yellow Group 10B. Basal Zone: Yellow Group 10A. When ¼ open, lower surface of petals: Yellow Group 10B. When ¼ open, outermost petals: Yellow Group 10D. Intonations of Yellow-Green Group 145B.

*Sepals*.—Color: Upper surface: Yellow-Green Group 146C. Lower surface: Yellow-Green Group 146B. Intonations: Greyed-Red Group 182B present on margins, apices and foliaceous appendages. Size: Average 22 to 24 mm (l)×6 to 7 mm (w). Calyx Diameter: 50 mm. Shape: Weak foliaceous appendages on 3 of the five sepals. Apex: Apiculate. Base: Flat at union with receptacle. Quantity: Five. Surface texture: Upper side: Hoary. Lower surface: Smooth, slightly pubescent. Margins: Cilliate. Stipitate glands: Limited numbers occasionally present on margins.

Flower bloom:

*Fragrance*.—Light to moderate.

*Duration*.—On the plant 12 to 16 days. Senesced petals drop away cleanly.

*Size*.—Large for a miniature rose. When open, the average flower diameter is 55 to 60 mm and the average flower height is 20 to 25 mm.

*Form*.—Shape: Rosette. Shape of flower when viewed from the side: Upon opening, upper part: Flattened convex. Upon opening, lower part: Flat. Open flower, upper part: Flat. Open flower, lower part: Flat.

Color:

*Upon opening, petals*.—Outermost petals: Outer Side: Yellow Group 10B. Inner Side: Marginal Zone: Yellow Group 10C. Middle Zone: Yellow Group 10C. Basal Zone: Yellow Group 10A. Innermost petals: Outer Side: Yellow-Orange Group 21A and 21B. Inner Side: Yellow Group 13A.

*Upon opening, basal petal spots*.—Basal petal spot, outermost petals: Outer Side: Yellow Group 12A. Inner Side: Yellow Group 12A. Size: Average 3 mm (h)×3 mm (w). Basal petal spot, innermost petals: No distinctive coloration at petal base observed.

*After opening, petals*.—Outermost petals: Outer Side: Yellow Group 10B. Inner Side: Marginal Zone: Yellow Group 10B. Middle Zone: Yellow Group 10B. Basal Zone: Yellow Group 10A. Innermost petals: Outer Side: Marginal Zone: Yellow Group 13B. Middle Zone: Yellow Group 13B. Basal Zone: Yellow Group 13A on the basal zone. Inner Side: Yellow Group 13A and Yellow-Orange Group 21B on the very innermost petals. No distinctive coloration at petal base observed after opening.

General tonality: On open flower Yellow Orange Group 15C. No change in the general tonality at the end of the $5^{th}$ day. Afterwards, general tonality is Yellow-Orange Group 14C.

Petals:

*Petal count*.—Very Double. Approximately 90 petals under normal conditions.

*Petal reflex*.—Outermost petals reflex very slightly. Reflex occurs one by one.

*Petal margin*.—Typically entire. Ruffled margins observed on very innermost petals.

*Petal shape*.—Obovate. Apex: Obtuse. Base: Cuneate.

*Petal size*.—13 to 28 mm (l)×10 to 30 mm (w).

*Petal arrangement*.—Not formal.

*Texture, outermost petals*.—Inner Side: Leathery. Outer Side: Leathery.

*Texture, innermost petals*.—Inner Side: Smooth. Outer Side: Smooth.

Petaloids:

*Petaloid count*.—Average of 10 per flower.

*Petaloid size*.—4 to 12 mm (l)×3 to 10 mm (w).

*Petaloid color*.—Inner side: Yellow-Orange Group 21A. Outer side: Orange Group 25B.

*Petaloid texture*.—Inner Side: Smooth. Outer Side: Smooth.

*Margins*.—Undulated.

*Petaloid shape*.—Most commonly obovate, with some petaloids highly irregular. Apex: Obtuse. Base: Both cuneate and attenuate petaloid bases observed.

Reproductive organs:

*Pistils*.—Abundant. Approximately 90 present. Stigmas: Location: Slightly superior in position to anthers. Color: Greyed-Yellow Group 161B. Diameter: 0.5 to 1 mm. Styles: Length: About 7 to 8 mm long. Color: Green-White Group 157D.

*Stamens*.—Approximately 80 on average and regularly arranged. Anthers: Size: Average 2 mm (l)×1 to 1.5 mm (w). Pollen: Generally present. Color: Yellow-Orange Group 15A. Filaments: Color: Yellow-Orange Group 15A. Length: 3 to 5 mm.

*Receptacle*.—Surface: Limited numbers of fine white hairs present. Color: Yellow-Green Group 144A.

Shape: Urn-shaped. Texture: Smooth, lightly pubescent. Size: 5 mm (h)×10 mm (w).

*Pedicel*.—Surface: With limited numbers of stipitate glands. Length: 40 to 45 mm average length. Diameter: 2.5 to 3 mm average diameter. Color: Yellow-Green Group 146B, with intonations of Greyed-Red Group 182A. Strength: Strong. Texture: Papillate. Borne: Typically singularly, multiple flower buds per inflorescence occasionally present, generally 2 to 3 per inflorescence if multiple. Below initiation of inflorescence, flowering laterals are absent. Generally 1 to 3 flowers per flowering shoot.

*Peduncle*.—Surface: With limited numbers of stipitate glands. Length: 25 to 45 mm average length. Diameter: 2.5 to 4 mm average diameter. Color: Yellow-Green Group 144A, with intonations of Greyed-Red Group 182A.. Strength: Strong. Texture: Papillate. Borne: Typically singularly, multiple flower buds per inflorescence occasionally present, generally 2 to 3 per inflorescence if multiple. Below initiation of inflorescence, flowering laterals are absent. Generally 1 to 3 flowers per flowering shoot.

THE PLANT

Growth: Moderately vigorous.

Plant habit: Compact. Bushy. When grown as a 10.5 cm pot plant, the average plant height is 22 to 28 cm and the average plant width is 20 cm.

Stems:

*Stem color*.—Young wood: Yellow-Green Group 144A. Older wood: Yellow-Green Group 146A.

*Stem surface texture*.—Young wood: Smooth. Older wood: Smooth.

*Length*.—19 to 26 mm average length when grown under commercial greenhouse floral production.

*Diameter*.—2.5 to 3 mm average diameter.

*Prickles*.—None observed on stems.

Leaves: Normally 5 leaflets on normal leaves in middle of the stem.

*Venation pattern*.—Pyramidal net pattern.

*Leaf size*.—95 to 110 mm (l)×65 to 70 mm (w).

*Abundance*.—Average number of leaves present.

Leaflets:

*Size*.—Average size of the terminal leaflet is 42 mm (l)×24 mm (w).

*Shape*.—Elliptic. Base: Obtuse. Apex: Acute.

*Margins*.—Serrated.

*Surface*.—Upper side of leaflet: Semi-glossy. Under side of leaflet: Matte.

*Texture*.—Upper side of leaflet: Smooth. Under side of leaflet: Leathery.

*Color, mature foliage*.—Upper Leaflet Surface: Green Group 139A. Lower Leaflet Surface: Greyed-Green Group 191A.

*Color, juvenile foliage*.—Upper Leaflet Surface: Yellow-Green Group 146A. Lower Leaflet Surface: Yellow-Green Group 146B.

*Anthocyanin intonation*.—Greyed-Purple 183A. Location: Anthocyanin intonation present on margins, petiole, midrib and underside of juvenile leaflets, and on margins of mature leaflets.

*Arrangement*.—Odd pinnate.

*Venation*.—Reticulate.

Stipules:

*Size*.—8mm (l)×3 to 4 mm (w).

*Stipule color*.—Yellow-Green Group 146A.

*Anthocyanin*.—Greyed-Red 182B, present on margins only.

*Stipitate glands*.—Limited numbers of stipitate glands present on margins only.

*Margins*.—Glandular toothed.

*Texture*.—Glabrous.

*Shape*.—Apex: Apiculate. Base: Winged.

Petiole:

*Length*.—Average 25 to 30 mm.

*Diameter*.—Average 1 mm.

*Petiole color*.—Upper Side: Yellow-Green Group 146A. Underneath: Yellow-Green Group 146B.

*Margins*.—With limited numbers of stipitate glands.

*Anthocyanin*.—Greyed-Purple 183D present on margins and underneath.

*Prickles*.—Small prickles occasionally present. Color: Yellow-Green Group 145C. Anthocyanin: Greyed-Red Group 182D. Shape: Linear. Average Length: 1.5 to 3 mm.

*Stipitate glands*.—Limited numbers of stipitate glands on margins and underneath.

*Texture*.—Upper Side: Papillate. Underneath: Glabrous.

Petiole rachis:

*Length*.—Average 15 to 20 mm.

*Diameter*.—Average 1 mm.

*Color*.—Upper Side: Yellow-Green Group 146B. Underneath: Yellow-Green Group 146C. Anthocyanin: Greyed-Purple 183A on margins, Greyed-Red Group 182D underneath.

*Margins*.—Occasional stipatite glands present.

*Prickles*.—A few small prickles underneath. Color: Yellow-Green Group 145C. Anthocyanin: Greyed-Red Group 182D. Shape: Linear. Average Length: 1.5 to 3 mm.

*Stipitate glands*.—Limited numbers of stipitate glands on margins and underneath.

Hips/seed formation: None observed.

Winter hardiness: Due to this variety's principle use in greenhouses, winter hardiness has not been evaluated.

Disease resistance: Above average resistance to Powdery mildew (*Sphaerotheca pannosa*) and *Botrytis* (*Botrytis cinerea*) diseases under normal greenhouse growing conditions in Jackson County, Oreg.

I claim:

1. A new and distinct variety of rose plant, as described and illustrated herein.

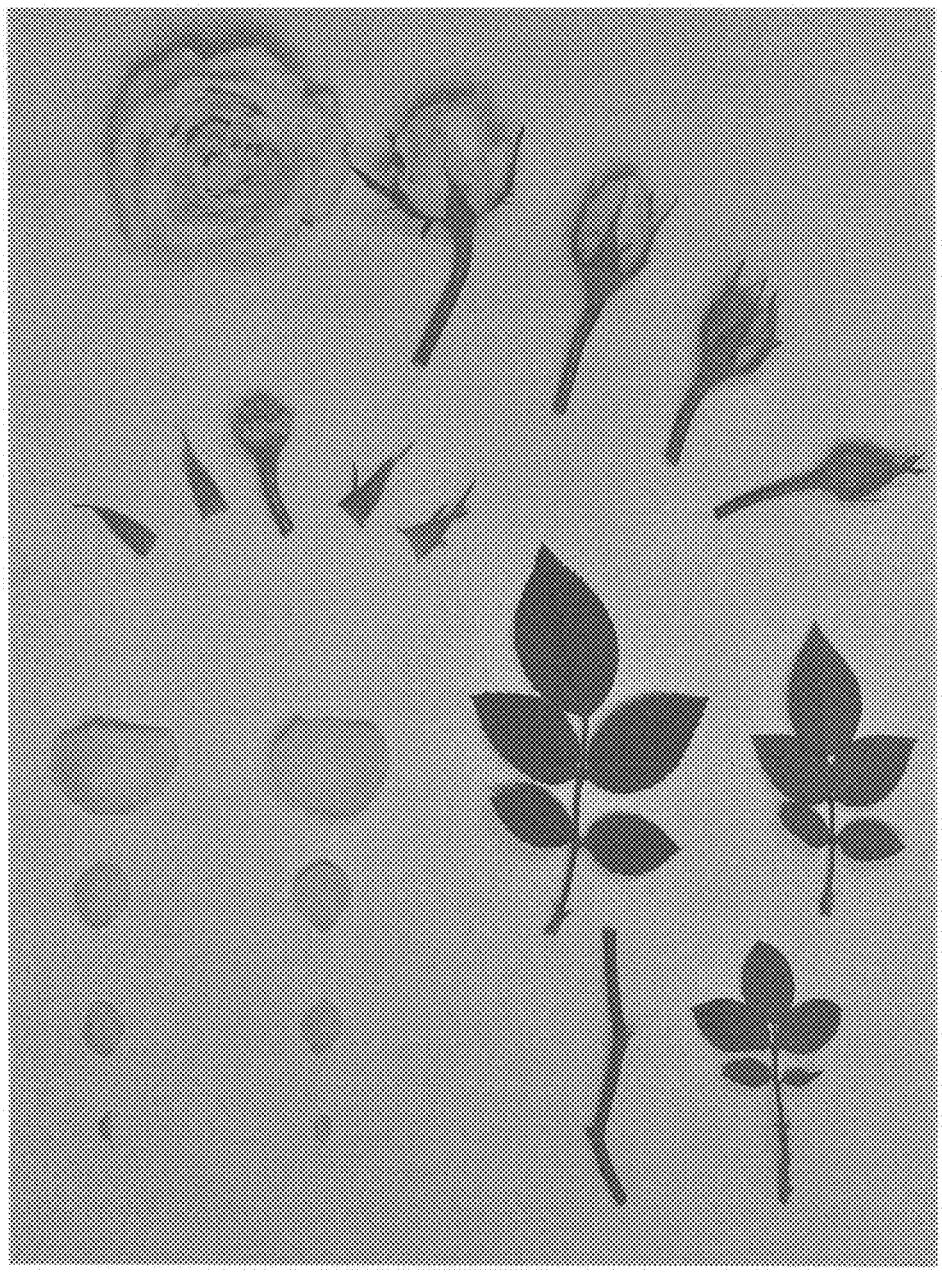

* * * * *